(12) United States Patent
Dalko

(10) Patent No.: US 9,029,422 B2
(45) Date of Patent: *May 12, 2015

(54) USE OF ((ETHOXY)HYDROXYPHENYL)ALKYL KETONE OR ETHOXYHYDROXYALKYLPHENOL COMPOUNDS FOR TREATING GREASY SKIN

(75) Inventor: Maria Dalko, Versailles (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/009,203

(22) PCT Filed: Mar. 30, 2012

(86) PCT No.: PCT/FR2012/050689
§ 371 (c)(1),
(2), (4) Date: Oct. 16, 2013

(87) PCT Pub. No.: WO2012/131272
PCT Pub. Date: Oct. 4, 2012

(65) Prior Publication Data
US 2014/0213660 A1    Jul. 31, 2014

(30) Foreign Application Priority Data
Apr. 1, 2011 (FR) .................................. 11 52794

(51) Int. Cl.
| | | |
|---|---|---|
| *A61K 31/12* | (2006.01) | |
| *A61K 31/045* | (2006.01) | |
| *A61K 8/34* | (2006.01) | |
| *A61Q 19/00* | (2006.01) | |
| *A61K 8/35* | (2006.01) | |
| *A61K 31/05* | (2006.01) | |

(52) U.S. Cl.
CPC .................. *A61K 8/347* (2013.01); *A61K 31/12* (2013.01); *A61K 31/05* (2013.01); *A61Q 19/008* (2013.01); *A61K 8/35* (2013.01)

(58) Field of Classification Search
CPC ........... A61K 8/18; A61K 8/347; A61K 8/35; A61K 31/05; A61K 31/12
USPC .................................................. 514/675, 728
See application file for complete search history.

(56) References Cited

U.S. PATENT DOCUMENTS
2010/0256100 A1    10/2010    Quedville et al.

FOREIGN PATENT DOCUMENTS
| | | |
|---|---|---|
| WO | WO 2012/130953 A1 | 10/2012 |
| WO | WO 2012/130954 A1 | 10/2012 |
| WO | WO 2012/131266 A1 | 10/2012 |
| WO | WO 2012/131272 A1 | 10/2012 |

OTHER PUBLICATIONS

U.S. Appl. No. 14/009,218, filed Oct. 1, 2013, Dalko, et al.
U.S. Appl. No. 14/007,565, filed Nov. 5, 2013, Dalko, et al.
U.S. Appl. No. 14/007,853, filed Nov. 5, 2013, Dalko, et al.
U.S. Appl. No. 14/007,549, filed Nov. 5, 2013, Chevalier, et al.
U.S. Appl. No. 14/007,520, filed Nov. 5, 2013, Chevalier, et al.

*Primary Examiner* — Kevin E Weddington
(74) *Attorney, Agent, or Firm* — Oblon, McClelland, Maier & Neustadt, L.L.P.

(57) ABSTRACT

The present invention relates to a cosmetic method for treating and/or preventing greasy skin or greasiness-prone skin and/or the associated cutaneous aesthetic defects, comprising the topical application to the skin of a composition comprising, in a cosmetically acceptable medium, at least one compound of formula (I):

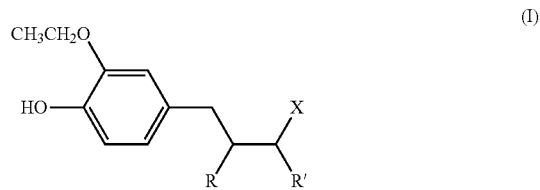

in which:
R represents a hydrogen atom or a saturated or unsaturated and linear or branched $C_1$-$C_6$ hydrocarbon radical;
R' represents a saturated or unsaturated and linear or branched $C_1$-$C_{18}$ hydrocarbon radical, optionally substituted by a hydroxyl group;
C—X represents C=O or CH—OH.

16 Claims, No Drawings

USE OF ((ETHOXY)HYDROXYPHENYL)ALKYL KETONE OR ETHOXYHYDROXYALKYLPHENOL COMPOUNDS FOR TREATING GREASY SKIN

The present invention relates to a cosmetic method for treating and/or preventing greasy skin or greasiness-prone skin and/or the associated cutaneous aesthetic defects, comprising the topical application to the skin of a composition comprising, in a cosmetically acceptable medium, at least one 4-(3-ethoxy-4-hydroxyphenyl)alkyl ketone or 2-ethoxy-4-hydroxyalkylphenol compound of formula (I) capable of being derived from vanillin.

The invention also relates to the cosmetic use of the said compounds as agents for treating and/or preventing greasy skin or greasiness-prone skin and/or the associated cutaneous aesthetic defects.

The term "the skin" means the entire skin of the body, including the scalp and mucous membranes.

Sebum normally constitutes a moisturizer for the epidermis and may be involved in the homeostasis of the epidermis, and especially in the proliferation and/or differentiation of epidermal cells.

It is the natural product from the sebaceous gland, which constitutes an appendix of the pilosebaceous unit. It is essentially a more or less complex mixture of lipids. Conventionally, the sebaceous gland produces squalene, triglycerides, aliphatic waxes, cholesterol waxes and possibly free cholesterol (Stewart, M. E., *Semin Dermatol,* 11, 100-105 (1992)). The action of bacterial lipases converts a variable proportion of the triglycerides formed into free fatty acids.

The sebocyte constitutes the competent cell of the sebaceous gland. The production of sebum is associated with a terminal differentiation programme of this cell. During this differentiation, the metabolic activity of the sebocyte is essentially centred on the biosynthesis of the lipids (lipogenesis) and more specifically on fatty acid neosynthesis.

Hyperseborrhoeic or greasy skin is characterized in particular by an excessive secretion and an excessive excretion of sebum. Conventionally, a sebum level of greater than 200 µg/cm² measured on the forehead is considered as being characteristic of such greasy skin.

Such skin is also often associated with a lack of desquamation, a glistening complexion, a thick skin texture, dilated pores or an irregular relief, which outward signs are experienced as skin imperfections or aesthetic defects. The appearance and/or visibility of the pores is also a characteristic of greasy skin. The shininess of the skin is also associated with the dilation of the pores, whence the interest in finding active agents for reducing the size of the dilated pores.

In order to combat hyperseborrhoea, various compounds have already been provided which, by topical application to the skin, are capable of reducing lipogenesis in the sebocytes and of consequently limiting the production of sebum. The treatments currently available for hyperseborrhoea are not entirely satisfactory, in particular with regard to the side effects which are frequently associated with them, such as irritant effects with certain topical agents, for example retinoids and benzoyl peroxides.

There thus remains a need to have available novel active agents which are capable of exerting a beneficial cosmetic action on greasy skin or greasiness-prone skin and/or the associated aesthetic defects.

There also remains a need to have available novel active agents which are capable of exerting a beneficial cosmetic action on greasy scalp conditions.

An object of the present invention is to satisfy these needs.

The Applicant Company has now discovered, surprisingly and unexpectedly, that the use of at least one compound of formula (I) according to the invention can prove to be useful in preventing and/or treating, effectively and without the abovementioned disadvantages, greasy skin or greasiness-prone skin and/or associated cutaneous aesthetic defects.

This discovery forms the basis of the invention.

A subject-matter of the present invention is thus a cosmetic method for treating and/or preventing greasy skin or greasiness-prone skin and/or the associated cutaneous aesthetic defects, comprising the topical application to the skin of a composition comprising, in a cosmetically acceptable medium, at least one compound of formula (I):

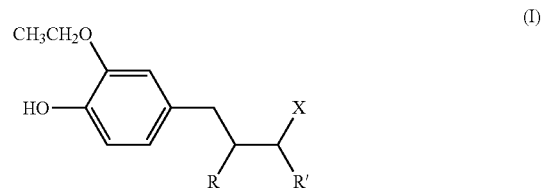

in which:
R represents a hydrogen atom or a saturated or unsaturated and linear or branched $C_1$-$C_6$ hydrocarbon radical;
R' represents a saturated or unsaturated and linear or branched $C_1$-$C_{18}$ hydrocarbon radical, optionally substituted by a hydroxyl group;
C—X represents C═O or CH—OH.

Another subject-matter of the present invention is the cosmetic use of at least one compound of formula (I):

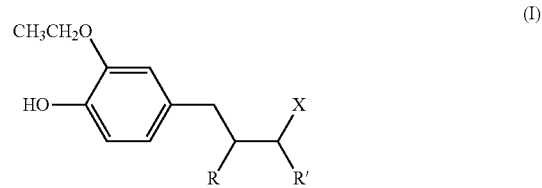

in which:
R represents a hydrogen atom or a saturated or unsaturated and linear or branched $C_1$-$C_6$ hydrocarbon radical;
R' represents a saturated or unsaturated and linear or branched $C_1$-$C_{18}$ hydrocarbon radical, optionally substituted by a hydroxyl group;
C—X represents C═O or CH—OH;
as agent for treating and/or preventing greasy skin or greasiness-prone skin and/or the associated cutaneous aesthetic defects.

According to this use, the compound of formula (I) is advantageously present in a composition comprising a cosmetically acceptable medium.

Within the meaning of the present invention, the term "preventing" is understood to mean the fact of reducing the risk or the probability of outward sign of a given phenomenon.

Indications

A compound of the invention may advantageously be used for the purpose of treating and/or preventing greasy skin or greasiness-prone skin and/or the associated cutaneous signs.

The invention is targeted at all of the skin of the body, including the scalp, and preferably the skin of the face, neckline, neck, arms and forearms, indeed even more preferably still the skin of the face (in particular of the forehead, nose, cheeks and chin), neckline and neck.

According to one embodiment, a cutaneous aesthetic defect may be chosen from skin imperfections due to hyperseborrhoea and/or a scalp disorder.

The cutaneous aesthetic signs of hyperseborrhoea, or greasy skin, which are more particularly considered by the invention may be glistening and/or thick skin and/or skin having follicular orifices or pores which are dilated, indeed even, in certain cases, which are filled with minute horny spicules or with comedones. Greasy skin is often associated with a lack of desquamation and with a thick skin texture.

The cutaneous aesthetic signs, or imperfections, of greasy skin or greasiness-prone skin may be chosen in particular from a thick skin texture, glistening or shiny skin, skin exhibiting dilated follicular orifices or pores, skin exhibiting follicular orifices or pores filled with horny spicules or with comedones, rough skin or skin exhibiting an irregular relief, or skin exhibiting an impairment of the complexion.

Greasy skin or greasiness-prone skin may also exhibit impairments of the complexion of the skin, such as a muddy, non-uniform or dull complexion.

Cosmetic Method

The invention relates to a cosmetic method dedicated in particular to individuals exhibiting greasy skin or greasiness-prone skin and/or associated cutaneous aesthetic defects.

An individual concerned by a cosmetic treatment method of the invention is naturally an individual exhibiting or liable to exhibit at least one of the cosmetic care indications defined previously.

A method of the invention makes it possible to treat greasy skin or greasiness-prone skin and in particular an aesthetic defect of the skin as defined previously.

Preferably, a method according to the invention will comprise the topical application of a composition according to the invention to the skin of the face, and/or the scalp.

The method according to the invention may prove to be very particularly of use:
 for preventing and/or treating aesthetic defects of greasy skin or greasiness-prone skin,
 for preventing and/or treating skin exhibiting dilated follicular orifices or pores, in particular for reducing the appearance and/or the visibility of the pores, in particular for narrowing the pores as/or reducing the size of the pores, and/or reducing the number of visible pores,
 for preventing and/or treating skin exhibiting follicular orifices or pores filled with horny spicules or comedones,
 for preventing and/or treating rough skin or skin exhibiting an irregular relief,
 for preventing and/or treating an impairment of the complexion of the skin, such as a muddy, non-uniform or dull complexion,
 for preventing and/or treating glistening or shiny skin (reducing the shininess of the skin),
 for preventing and/or treating an aesthetic defect of the scalp related to excessive excretion and/or secretion of sebum, or
 for improving the comfort of the skin or the scalp.

All these indications can be easily measured by a person skilled in the art, according to well-known techniques.

The appearance and/or the visibility of the pores can be measured by techniques known to a person skilled in the art and in particular according to the directions published in Application WO2011/114010. By way of example, the size of the pores can be measured using the Dermascore® device, according to the protocol described in the paper: Quantification of facial pores using image analysis, Ghislain François et al., Cosmetic Dermatology, Vol. 22, No. 9, pages 457-463.

The measurement of the appearance and/or the visibility of the pores can also be carried out by measuring the size of the pores on the forehead at different days of the treatment on each half-face treated with a composition comprising the active agent (versus half-face treated with placebo), recording, using a scale having 4 values:
Value=0: no pores observed
Value=1: small-sized pores observed
Value=2: medium-sized pores observed
Value=3: large-sized pores observed.
It is thus possible to calculate the difference in values Δ obtained between the value recorded for the half-face treated with the active agent and the value recorded for the half-face treated with the placebo.

The glistening or shininess of the skin can be measured by techniques known to a person skilled in the art and in particular according to the directions published in Applications FR 2 881 643 B1 and FR 2 952 299 B1. By way of example, the glistening can be evaluated visually, on the forehead, at different days of the treatment (total of 45 days), on each half-face treated with a composition comprising the active agent (versus half-face treated with placebo), recording, using a scale having 4 values:
Value=0: no glistening observed
Value=1: slight glistening
Value=2: moderate glistening
Value=3: strong glistening.
It is thus possible to calculate the difference in values Δ obtained between the value recorded for the half-face treated with the active agent and the value recorded for the half-face treated with the placebo.

The mattifying (less shiny) effect can also be evaluated using a gonioreflectometer, by measuring the ratio R of the specular reflection to the diffuse reflection. A value for R of less than or equal to 2 generally expresses a mattifying effect.

The complexion of the skin can be measured by techniques known to a person skilled in the art and in particular according to the directions published in Example 1 of Application WO2011/070508. By way of example, the luminosity of the complexion of the face can be evaluated visually by an investigating dermatologist after application of the composition comprising the active agent versus placebo, according to a scale from 0 to 4 (0=highly radiant; 1=radiant; 2=neither dull/nor radiant; 3=dull; 4=very dull).

Compounds of Formula (I)

The compounds according to the invention thus correspond to the formula (I):

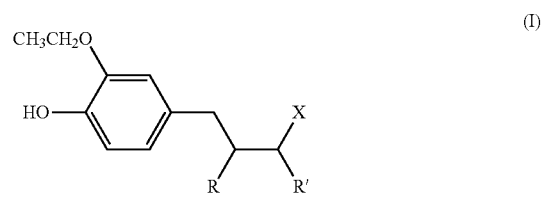

in which:
 R represents a hydrogen atom or a saturated or unsaturated (alkyl or alkenyl) and linear or branched $C_1$-$C_6$ hydrocarbon radical;

R' represents a saturated or unsaturated (alkyl or alkenyl) and linear or branched $C_1$-$C_{18}$ hydrocarbon radical, optionally substituted by a hydroxyl group;

C—X represents C=O or CH—OH.

Preferably, R represents H, methyl or ethyl.

Preferably, R' represents a saturated linear $C_1$-$C_6$ or unsaturated linear $C_2$-$C_6$ hydrocarbon radical, optionally substituted by a hydroxyl group.

Preferably, the compounds correspond to the formula (I), in which:
- C—X represents C=O, R=H and R' represents a linear $C_1$-$C_6$ alkyl radical, optionally substituted by an OH; preferably, R'=methyl or ethyl; or else
- C—X represents CH—OH, R=H and R' represents a linear $C_1$-$C_6$ alkyl radical, optionally substituted by an OH; preferably, R'=methyl or ethyl.

Mention may in particular be made of the following compounds (1), (2) and (3):

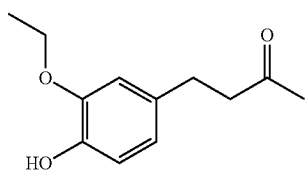

4-(3-ethoxy-4-hydroxyphenyl)butan-2-one (1)

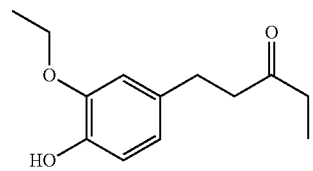

5-(3-ethoxy-4-hydroxyphenyl)pentan-3-one (2)

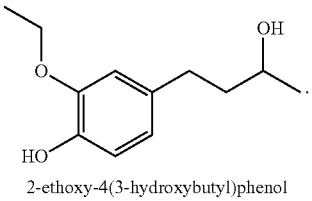

2-ethoxy-4(3-hydroxybutyl)phenol (3)

Preference will be given to the compound (1):

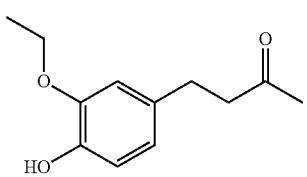

4-(3-ethoxy-4-hydroxyphenyl)butan-2-one (1)

A mixture of compounds of formula (I) may, of course, be used.

The compounds of formula (I) can be easily prepared by a person skilled in the art on the basis of his general knowledge. Mention may in particular be made of the following bibliographic references: J. Asian Natural Products Research, 2006, 8(8), 683-688; Helv. Chimica Acta, 2006, 89(3), 483-495; Chem. Pharm. Bull., 2006, 54(3), 377-379; and Bioorg. Med. Chem. Lett., 2004, 14(5), 1287-1289.

They can thus be prepared from ethylvanillin, in the following way:

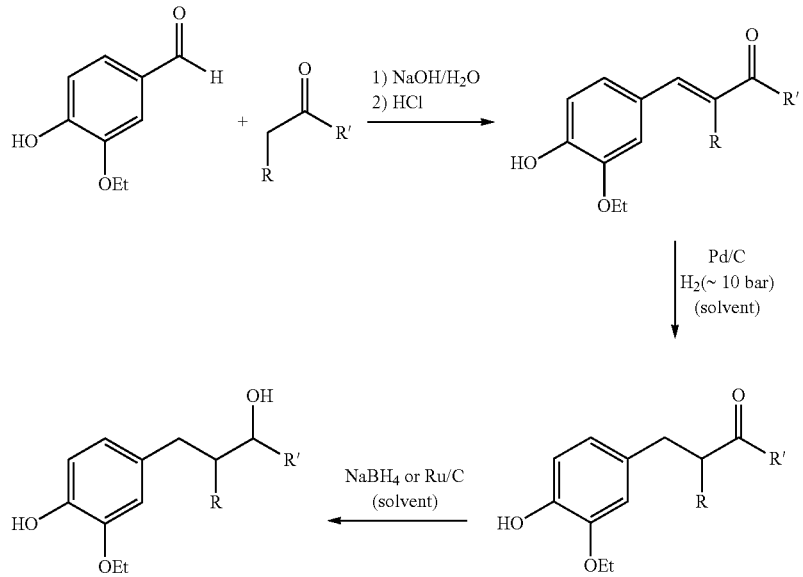

The compounds of formula (I) with C—X representing CHOH can be obtained by reduction of the corresponding compounds in which C—X represents C=O, for example by reduction with Ru/C or NaBH$_4$.

The compounds of formula (I), alone or as a mixture, can be used in a proportion of from 0.1% to 10% by weight, in particular from 0.5% to 5% by weight, with respect to the total weight of the composition in which they are present.

Composition

The composition according to the present invention is advantageously cosmetic.

The composition can be a care and/or cleansing and/or scrubbing and/or make-up composition intended to be rinsed off or left on. Preferably, it will be a leave-on care composition. When the composition comprises exfoliants or abrasive fillers, it will preferably be a rinse-off composition.

The compositions according to the invention are advantageously intended for a topical application to the face (in particular the forehead, nose, cheeks or chin) and/or the scalp.

The composition according to the invention comprises a cosmetically acceptable medium, that is to say a medium which is compatible with the skin, nails, mucous membranes, tissues and hair, which has no unpleasant odour, colour or appearance, and which does not cause any stinging, tautness or redness which is unacceptable to the user.

Preferably, the said medium comprises water and/or one or more cosmetically acceptable organic solvents. The organic solvents can be chosen from linear or branched $C_1$-$C_6$ monoalcohols, such as ethanol, isopropanol, tert-butanol or n-butanol; polyols, such as glycerol, propylene glycol, hexylene glycol (or 2-methyl-2,4-pentanediol) and polyethylene glycols; polyol ethers, such as dipropylene glycol monomethyl ether; and their mixtures.

Preferably, the cosmetic composition used according to the invention comprises an amount of organic solvents ranging from 0.05% to 60%, preferably from 0.5% to 50% and even better still from 1% to 40% by weight, with respect to the total weight of the cosmetic composition.

According to a preferred embodiment of the invention, the composition has a pH preferably close to that of the skin, of between 4 and 7.

The compositions according to the invention can be provided in all the formulation forms conventionally used for a topical application and in particular in the form of aqueous or aqueous/alcoholic solutions, of oil-in-water (O/W), water-in-oil (W/O) or multiple (triple: W/O/W or O/W/O) emulsions, of aqueous gels or of dispersions of a fatty phase in an aqueous phase using spherules, it being possible for these spherules to be lipid vesicles of ionic and/or non-ionic type (liposomes, niosomes or oleosomes). These compositions are prepared according to the usual methods.

In addition, the composition according to the invention can be more or less fluid and can have the appearance of a white or coloured cream, an ointment, a milk, a lotion, a serum, a paste, a foaming gel, a care product, a toner or a foam. It can optionally be applied to the skin in aerosol form. It can also be provided in solid form, for example in the form of a stick.

When the composition used according to the invention comprises an oily phase, it preferably comprises at least one oil. It can additionally comprise other fatty substances.

Mention may be made, as oils which can be used in the composition of the invention, for example, of:

hydrocarbon oils of animal origin, such as perhydrosqualene;

hydrocarbon oils of vegetable origin, such as liquid triglycerides of fatty acids comprising from 4 to 10 carbon atoms, such as heptanoic or octanoic acid triglycerides, or alternatively, for example, sunflower oil, maize oil, soybean oil, cucumber oil, grapeseed oil, sesame oil, hazelnut oil, apricot oil, macadamia oil, arara oil, castor oil, avocado oil, caprylic/capric acid triglycerides, such as those sold by Stearineries Dubois or those sold under the names Miglyol 810, 812 and 818 by Dynamit Nobel, jojoba oil or shea butter oil;

synthetic esters and ethers, in particular of fatty acids, such as the oils of formulae R'COOR$^2$ and R'OR$^2$ in which R' represents the residue of a fatty acid comprising from 8 to 29 carbon atoms and R$^2$ represents a branched or unbranched hydrocarbon chain comprising from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; and pentaerythritol esters, such as pentaerythrityl tetraisostearate;

linear or branched hydrocarbons of mineral or synthetic origin, such as liquid paraffins, which are volatile or non-volatile, and their derivatives, petrolatum, polydecenes or hydrogenated polyisobutene, such as Parleam oil;

fatty alcohols having from 8 to 26 carbon atoms, such as cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils, such as those described in the document JP-A-2-295 912;

silicone oils, such as volatile or non-volatile polymethylsiloxanes (PDMSs) with a linear or cyclic silicone chain, which are liquid or pasty at ambient temperature, in particular cyclopolydimethylsiloxanes (cyclomethicones), such as cyclohexasiloxane;

polydimethylsiloxanes comprising alkyl, alkoxy or phenyl groups, which are pendent or at the end of the silicone chain, which groups have from 2 to 24 carbon atoms; or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes, (2-phenylethyl)trimethylsiloxysilicates and polymethylphenylsiloxanes;

their mixtures.

In the list of the abovementioned oils, hydrocarbon oil is understood to mean any oil predominantly comprising carbon and hydrogen atoms, and optionally ester, ether, fluoro, carboxylic acid and/or alcohol groups.

The other fatty substances which can be present in the oily phase are, for example, fatty acids comprising from 8 to 30 carbon atoms, such as stearic acid, lauric acid, palmitic acid and oleic acid; waxes, such as lanolin wax, beeswax, carnauba wax or candelilla wax, paraffin wax, lignite wax or microcrystalline waxes, ceresin or ozokerite, or synthetic waxes, such as polyethylene waxes or Fischer-Tropsch waxes; silicone resins, such as trifluoromethyl-$C_{1-4}$-alkyl dimethicone and trifluoropropyl dimethicone; and silicone elastomers, such as the products sold under the KSG name by Shin-Etsu, under the Trefil, BY29 or EPSX names by Dow Corning or under the Gransil name by Grant Industries.

These fatty substances can be chosen in a varied way by a person skilled in the art in order to prepare a composition having the desired properties, for example of consistency or texture.

According to a specific embodiment of the invention, the composition according to the invention is a water-in-oil (W/O) or oil-in-water (O/W) emulsion. The proportion of the oily phase of the emulsion can range from 5% to 80% by weight and preferably from 5% to 50% by weight, with respect to the total weight of the composition.

The emulsions generally comprise at least one emulsifier chosen from amphoteric, anionic, cationic or non-ionic emulsifiers, used alone or as a mixture, and optionally a co-emulsifier. The emulsifiers are appropriately chosen according to the emulsion to be obtained (W/O or O/W). The emulsifier and the co-emulsifier are generally present in the composition in a proportion ranging from 0.3% to 30% by weight and preferably from 0.5% to 20% by weight, with respect to the total weight of the composition.

Mention may be made, for W/O emulsions, for example, as emulsifiers, of dimethicone copolyols, such as the mixture of cyclomethicone and dimethicone copolyol sold under the name DC 5225 C by Dow Corning, and alkyl dimethicone copolyols, such as the lauryl methicone copolyol sold under the name Dow Corning 5200 Formulation Aid by Dow Corning and the cetyl dimethicone copolyol sold under the name Abil EM $90^R$ by Goldschmidt. Use may also be made, as surfactant for W/O emulsions, of a solid crosslinked organopolysiloxane elastomer comprising at least one oxyalkylenated group, such as those obtained according to the procedure of Examples 3, 4 and 8 of the document U.S. Pat. No. 5,412,004 and of the examples of the document U.S. Pat. No. 5,811,487, in particular the product of Example 3 (synthesis example) of Patent U.S. Pat. No. 5,412,004, and such as the product sold under the reference KSG 21 by Shin-Etsu.

Mention may be made, for the O/W emulsions, for example, as emulsifiers, of non-ionic emulsifiers, such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) esters of fatty acids;

oxyalkylenated (oxyethylenated and/or oxypropylenated) ethers of fatty alcohols; sugar esters, such as sucrose stearate; and their mixtures, such as the mixture of glyceryl stearate and PEG-40 stearate.

The composition according to the invention can also comprise adjuvants which are customary in the cosmetics field, such as hydrophilic or lipophilic gelling agents, preservatives, water, solvents, fragrances, fillers, UV-screening agents, odour absorbers, colourants, basic agents, acids, or non-ionic, anionic or cationic surfactants.

The amounts of these various adjuvants are those conventionally used in the field under consideration, for example from 0.01% to 20% of the total weight of the composition. Depending on their nature, these adjuvants can be introduced into the fatty phase, into the aqueous phase and/or into the lipid vesicles.

Mention may be made, as fillers which can be used in the composition of the invention, for example, in addition to pigments, of silica powder; talc; polyamide particles and in particular those sold under the name Orgasol by Atochem; polyethylene powders; microspheres based on acrylic copolymers, such as those made of ethylene glycol dimethacrylate/lauryl methacrylate copolymer sold by Dow Corning under the name Polytrap; expanded powders, such as hollow microspheres and in particular the microspheres sold under the name Expancel by Kemanord Plast or under the name Micropearl F 80 ED by Matsumoto; silicone resin microbeads, such as those sold under the name Tospearl by Toshiba Silicone; and their mixtures.

Mention may in particular be made, as hydrophilic or lipophilic gelling agents, of carbopols, luvigels, Hostacerin AMPS, Simulgel, Sepigels, xanthan gum, guar gum, cellulose gum, alginates and their mixtures. Mention may also be made of hectorites.

Of course, a person skilled in the art will take care to choose this or these optional additional ingredients and/or active agents, and/or their amounts, such that the advantageous properties of the compound of formula (I) according to the invention are not, or not substantially, detrimentally affected by the envisaged addition.

The compositions according to the invention can be applied directly to the skin or, alternatively, to cosmetic supports of occlusive or non-occlusive type intended to be applied locally to the skin. Mention may in particular be made, as non-limiting examples of cosmetic supports, of a patch, a wipe, a roll-on and a pen.

The composition according to the present invention will comprise, according to a specific embodiment, in addition to the compound of formula (I), at least one additional active agent for the care of greasy skin or greasiness-prone skin.

Additional Active Agents for the Care of Greasy Skin:

In the context of the present invention, the expression "additional active agent for the care of greasy skin" is understood to mean a compound which has, by itself, that is to say not requiring the intervention of an external agent to activate it, a biological activity which can in particular be:

a desquamating activity (which allows the comedones to open), and/or an antimicrobial activity (in particular on P. acnes), and/or a soothing or anti-inflammatory activity, and/or a sebum-regulating activity, and/or an antioxidant activity (which prevents squalene from being oxidized and comedones from being formed)

a healing activity an astringent activity.

The additional active agent for the care of greasy skin which can be used in the compositions of the invention is preferably chosen from desquamating agents, antimicrobial agents, soothing agents, anti-inflammatory agents, sebum-regulating agents, antioxidants, healing agents, astringents, and their mixtures.

The additional active agent for the care of greasy skin used in the composition according to the invention can represent from 0.0001% to 20%, preferably from 0.01% to 10% and better still from 0.01% to 5% by weight, with respect to the total weight of the composition.

According to one embodiment, a composition according to the invention will not comprise essential oil.

The invention is illustrated in greater detail in the following examples.

The example which follows illustrates the invention without limiting the scope thereof. The compounds are, as the case may be, mentioned as chemical names or as CTFA (International Cosmetic Ingredient Dictionary and Handbook) names.

EXAMPLE

Treating Lotion for Greasy Skin

The amounts are given as percentage by weight, with respect to the total weight of the composition.

| | |
|---|---|
| Vitamin E | 0.05% |
| Myrtrimonium bromide | 0.03% |
| Disodium EDTA | 0.08% |
| PEG-8 | 5.0% |
| Glycerol | 3.0% |
| PEG-60 hydrogenated castor oil | 0.5% |
| 4-(3-Ethoxy-4-hydroxyphenyl)butan-2-one (compound (1) according to the invention) | 2% |
| Isopropyl N-lauroylsarcosinate* | 1.4% |
| Preservatives | 0.8% |
| Fragrance | 0.08% |
| Water | q.s. for 100% |

*Eldew ® SL 205 from Ajinomoto

This composition, applied to the skin, makes it possible to treat and/or prevent greasy skin or greasiness-prone skin and/or the associated cutaneous aesthetic defects as described in the present patent application.

The invention claimed is:

1. A method for treating greasy skin, comprising topically applying to the skin a composition comprising, in a cosmetically acceptable medium, at least one compound of formula (I):

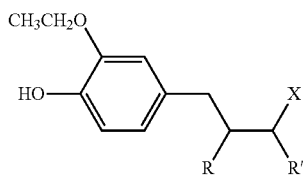

(I)

wherein:
R is a hydrogen atom or a saturated or unsaturated and linear or branched $C_1$-$C_6$ hydrocarbon radical;
R' is a saturated or unsaturated and linear or branched $C_1$-$C_{18}$ hydrocarbon radical, optionally substituted by a hydroxyl group; and
C—X is CO=O or CH—OH.

2. The method according to claim 1, wherein R is H, methyl or ethyl.

3. The method according to claim 1, wherein R' is a saturated linear $C_1$-$C_6$ or unsaturated linear $C_2$-$C_6$ hydrocarbon radical, optionally substituted by a hydroxyl group.

4. The method according to claim 1, wherein either:
C—X is C=O, R=H and R' is a linear $C_1$-$C_6$ alkyl radical, optionally substituted by an OH; or
C—X is CH—OH, R=H and R' is a linear $C_1$-$C_6$ alkyl radical, optionally substituted by an OH.

5. The method according to claim 1, wherein the compound is at least one selected from the group consisting of:

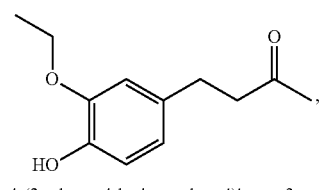

(1)

4-(3-ethoxy-4-hydroxyphenyl)butan-2-one

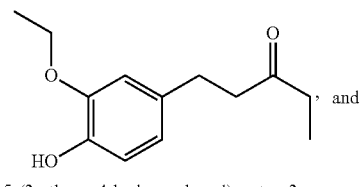

(2)

5-(3-ethoxy-4-hydroxyphenyl)pentan-3-one

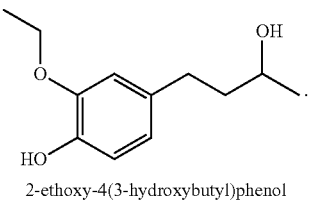

(3)

2-ethoxy-4(3-hydroxybutyl)phenol

6. The method according to claim 5, wherein the compound is

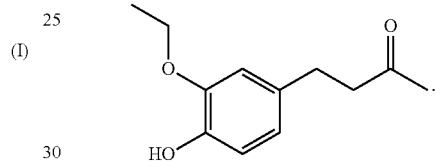

(1)

4-(3-ethoxy-4-hydroxyphenyl)butan-2-one

7. The method according to claim 1, wherein the at least one compound is present in an amount of from 0.1% to 10% by weight, with respect to a total weight of the composition.

8. The method according to claim 1, wherein C—X is C=O, R=H and R' is a linear $C_1$-$C_6$ alkyl radical, optionally substituted by an OH.

9. The method according to claim 1, wherein C—X is CH—OH, R=H and R' is a linear $C_1$-$C_6$ alkyl radical, optionally substituted by an OH.

10. The method according to claim 1, wherein C—X is C=O, R=H and R' is a linear $C_1$-$C_6$ alkyl radical, optionally substituted by an OH.

11. The method according to claim 1, wherein either:
C—X is C=O, R=H and R' is methyl or ethyl, optionally substituted by an OH; or C—X is CH—OH, R=H and R' is methyl or ethyl, optionally substituted by an OH.

12. The method according to claim 1, wherein the at least one compound is present in an amount of from 0.5% to 5% by weight, with respect to a total weight of the composition.

13. The method according to claim 5, wherein the at least one compound is present in an amount of from 0.1% to 10% by weight, with respect to a total weight of the composition.

14. The method according to claim 6, wherein the at least one compound is present in an amount of from 0.1% to 10% by weight, with respect to a total weight of the composition.

15. The method according to claim 5, wherein the at least one compound is present in an amount of from 0.5% to 5% by weight, with respect to a total weight of the composition.

16. The method according to claim 6, wherein the at least one compound is present in an amount of from 0.5% to 5% by weight, with respect to a total weight of the composition.

* * * * *